(12) United States Patent
Kang et al.

(10) Patent No.: US 11,315,413 B2
(45) Date of Patent: *Apr. 26, 2022

(54) TRAFFIC ACCIDENT ANALYSIS SYSTEM USING ERROR MONITORING

(71) Applicants: HYUNDAI MOTOR COMPANY, Seoul (KR); KIA MOTORS CORPORATION, Seoul (KR); SOOKMYUNG WOMEN'S UNIVERSITY INDUSTRY—ACADEMIC COOPERATION FOUNDATION, Seoul (KR)

(72) Inventors: Jeong Su Kang, Seongnam-si (KR); Suh Yeon Dong, Seoul (KR)

(73) Assignees: Hyundai Motor Company, Seoul (KR); Kia Motors Corporation, Seoul (KR); Sookmyung Women's University Industry-Academic Cooperation Foundation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/925,739

(22) Filed: Jul. 10, 2020

(65) Prior Publication Data
US 2021/0074149 A1   Mar. 11, 2021

(30) Foreign Application Priority Data
Sep. 5, 2019 (KR) .................. 10-2019-0110108

(51) Int. Cl.
*G08G 1/01* (2006.01)
*G08G 1/052* (2006.01)
*A61B 5/369* (2021.01)

(52) U.S. Cl.
CPC ........... *G08G 1/0137* (2013.01); *G08G 1/052* (2013.01); *A61B 5/369* (2021.01); *A61B 2503/22* (2013.01)

(58) Field of Classification Search
CPC ........ A61B 5/377; A61B 5/18; G08G 1/0137; G08G 1/052; G05D 1/0088; B60W 30/00
See application file for complete search history.

(56) References Cited

U.S. PATENT DOCUMENTS

| | | | |
|---|---|---|---|
| 2014/0128763 A1* | 5/2014 | Fadem | A61B 5/165 600/544 |
| 2014/0308978 A1* | 10/2014 | Herz | G08G 1/096 455/456.3 |

(Continued)

*Primary Examiner* — Mirza F Alam
(74) *Attorney, Agent, or Firm* — Mintz Levin Cohn Ferris Glovsky and Popeo, P.C.; Peter F. Corless

(57) ABSTRACT

An error monitoring apparatus and method are provided. The error monitoring method includes determining whether or not a predetermined event has occurred to a first mobility; sensing to collect an event-related potential (ERP) for at least one passenger of the first mobility for a predetermined amount of time, analyzing the collected ERP based on the determination, and transmitting error information of the first mobility to a traffic control server based on an analysis result. Herein, the predetermined event includes a traffic accident related at least to the first mobility, and the error information of the first mobility includes at least one of time information regarding when the ERP occurs, a waveform of the ERP, location information of the first mobility, or operational information of the first mobility.

16 Claims, 13 Drawing Sheets

(56) References Cited

U.S. PATENT DOCUMENTS

2019/0212736 A1* 7/2019 Jang ............... G05D 1/0088
2019/0286793 A1* 9/2019 Patton ............. G06F 21/554
2021/0041953 A1* 2/2021 Poltorak .......... G16H 40/63

* cited by examiner

FIG. 4A
FIG. 4B
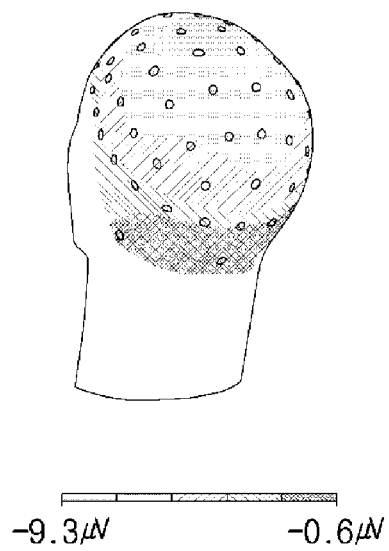
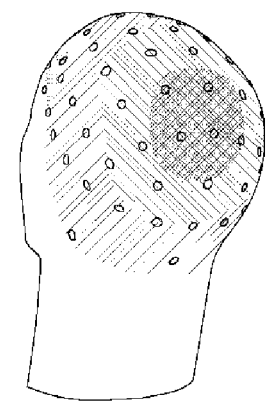
-9.3µV   -0.6µV
-1.8µV   13.0µV

TRAFFIC ACCIDENT ANALYSIS SYSTEM USING ERROR MONITORING

CROSS REFERENCE TO RELATED APPLICATION

The present application claims priority to and the benefit of Korean Patent Application No. 10-2019-0110108, filed Sep. 5, 2019, which is incorporated herein by reference in its entirety.

TECHNICAL FIELD

The present disclosure relates to a mobility controlling method and apparatus. More particularly, the present disclosure relates to a mobility controlling method and apparatus based on error monitoring.

BACKGROUND

The statements in this section merely provide background information related to the present disclosure and may not constitute prior art.

As one of the transport means, a vehicle (or mobility) is a very important means and tool for living a life in the modern world. Furthermore, a vehicle itself may be regarded as something special that gives meaning to someone.

As technology is advanced, functions provided by a vehicle also gradually evolve. For example, in recent years, vehicles not only transport a passenger to a destination, but also meet a passenger's needs for faster and safer travel to a destination. In addition, new devices are being added to a vehicle system in order to satisfy a passenger's aesthetic taste and comfort. In addition, the existing devices like steering wheels, transmissions and acceleration/deceleration devices are also being developed so that more functions can be provided to users.

Meanwhile, a brain-computer interface or a brain-machine interface is a field of controlling a computer or a machine according to a person's intention by using brain wave signals. ERP (Event-Related Potential) is closely related to cognitive functions.

SUMMARY

The present disclosure provides a traffic accident analysis system.

The present disclosure also provides a traffic accident analysis system that determines primary responsibility for a traffic accident between mobilities on the basis of error monitoring.

Yet, the present disclosure provides an error monitoring apparatus and method performing error monitoring.

Yet, the present disclosure provides a traffic control server determining primary responsibility for a traffic accident between mobilities on the basis of error monitoring and an operation method thereof.

The present disclosure may provide an error monitoring apparatus including a detecting unit determining whether or not a predetermined event has occurred to a first mobility, a sensing unit collecting an event-related potential for at least one passenger of the first mobility for a predetermined time, an analyzer analyzing the event-related potential collected for the predetermined time on the basis of the determination, and a transmitter sending error information of the first mobility to a traffic control server on the basis of the analysis result. The predetermined event includes a traffic accident at least related to the first mobility, and the error information of the first mobility includes at least one of time information regarding the onset of the event-related potential, a waveform of the event-related potential, location information of the first mobility, and operational information of the first mobility.

According to one embodiment, the sensing unit may further include at least one of a speed measuring unit, an image acquisition unit, a sound acquisition unit, a wheel monitoring unit, and a manipulation apparatus unit, which are included in the first mobility.

According to one embodiment, the speed measuring unit may measure at least one of a speed and a direction of the first mobility, and the detecting unit may determine that the predetermined event has occurred to the first mobility, when at least one of the measured speed and the measured direction exceeds a predetermined threshold within a predetermined time range.

According to one embodiment, the image acquisition unit may monitor a distance between the first mobility and an object that is different from the first mobility, and the detecting unit may determine that the predetermined event has occurred to the first mobility, when the distance becomes below a predetermined threshold within a predetermined time range.

According to one embodiment, the sound acquisition unit may acquire a sound generated from at least one of the inside and the outside of the first mobility, and the detecting unit may determine that the predetermined event has occurred to the first mobility, when a volume of the sound exceeds a predetermined threshold within a predetermined time range.

According to one embodiment, the wheel monitoring unit may monitor at least one level of a temperature and a pressure inside a wheel of the first mobility, and the detecting unit may determine that the predetermined event has occurred to the first mobility, when the level exceeds a predetermined threshold within a predetermined time range.

According to one embodiment, the manipulation apparatus unit may monitor a pressure upon at least one of a steering wheel, an accelerator pedal, and a brake of the first mobility, and the detecting unit may determine that the predetermined event has occurred to the first mobility, when a magnitude of the pressure exceeds a predetermined threshold within a predetermined time range.

According to one embodiment, the detecting unit may determine whether or not the predetermined event has occurred to the first mobility by applying a predetermined threshold to at least one among the speed measuring unit, the image acquisition unit, the sound acquisition unit, the wheel monitoring unit, and the manipulation apparatus unit. The predetermined threshold is a value set by a user input or a predefined value. A magnitude of the predetermined threshold may be set according to the speed measuring unit, the image acquisition unit, the sound acquisition unit, the wheel monitoring unit, and the manipulation apparatus unit, respectively.

According to one embodiment, the event-related potential (ERP) may include at least one of error-related negativity (ERN) and error positivity (Pe).

According to one embodiment, the event-related potential (ERP) may further include at least one of correct-related negativity (CRN) and correct positivity (Pc).

According to one embodiment, the analysis may compare an amplitude of an event-related potential, which is collected for the predetermined time, and a predetermined threshold.

According to one embodiment, the predetermined threshold may be differently determined according to at least one of a type of the ERP and a passenger from whom the ERP is obtained.

According to one embodiment, when the amplitude of the ERP collected for the predetermined time range exceeds the predetermined threshold range, the transmitter may transmit error information of the first mobility to the traffic control server.

In addition, the present disclosure may provide a traffic control server that includes a receiver receiving error information of a first mobility from the first mobility and a controller determining a degree of responsibility for a first event occurring to the first mobility on the basis of the error information of the first mobility. The first event includes a traffic accident at least related to the first mobility. The error information of the first mobility includes at least one of time information regarding when an event-related potential for at least one passenger in the first mobility occurs, a waveform of the event-related potential, location information of the first mobility, and operational information of the first mobility.

According to one embodiment, the controller may identify a first event occurring to the first mobility by using error information of the first mobility.

According to one embodiment, the controller may further obtain information related to the first event from an image acquisition unit that is installed within a predetermined range around a location of the first mobility and identify the first event occurring to the first mobility by using the obtained information and the error information of the first mobility.

According to one embodiment, the receiver may further receive error information of at least one second mobility from the second mobility that is different from the first mobility, and the controller may further include identifying a second event occurring to the second mobility by using the error information of the second mobility and selecting a second mobility related to the first event on the basis of the identified second event.

According to one embodiment, the controller may select a second mobility to which the second event occurs, when the second event is the same as the first event.

According to one embodiment, the controller may further include determining a degree of responsibility for the occurrence of the first event between the first mobility and the selected second mobility.

According to one embodiment, the degree of responsibility may be proportional to a peak value of ERP of the first mobility and a peak value of ERP of the second mobility.

In addition, the present disclosure may provide a traffic accident analysis system that includes an error monitoring apparatus transmitting error information of a mobility to a server and a traffic control server determining a degree of responsibility for a predetermined event between mobilities by using the error information of a mobility. The error monitoring apparatus determines whether or not a predetermined event has occurred to a first mobility, collects an event-related potential for at least one passenger of the first mobility for a predetermined time, analyzes the event-related potential collected for the predetermined time on the basis of the determination, and transmits the error information of the first mobility to the traffic control server on the basis of the analysis result. The traffic control server receives the error information of the first mobility from the monitoring apparatus and determines a degree of responsibility for a first event occurring to the first mobility. The predetermined event includes at least a traffic event related to the first mobility. The error information of the first mobility includes at least one of time information regarding the onset of the event-related potential, a waveform of the event-related potential, location information of the first mobility, and operational information of the first mobility.

According to one embodiment, the traffic control server may further include further receiving error information of at least one second mobility from the second mobility that is different from the first mobility, identifying a second event occurring to the second mobility by using error information of the second mobility, selecting a second mobility with a second event that is the same as the first event, and determines a degree of responsibility for the first event between the first mobility and the selected second mobility.

According to one embodiment, the degree of responsibility may be proportional to a peak value of ERP of the first mobility and a peak value of ERP of the second mobility.

In addition, the present disclosure may provide an error monitoring method including determining whether or not a predetermined event has occurred to a first mobility, sensing to collect an event-related potential for at least one passenger of the first mobility for a predetermined time, analyzing the event-related potential collected for the predetermined time on the basis of the determination, and transmitting error information of the first mobility to a traffic control server on the basis of the analysis result. The predetermined event includes a traffic accident at least related to the first mobility, and the error information of the first mobility includes at least one of time information regarding the onset of the event-related potential, a waveform of the event-related potential, location information of the first mobility, and operational information of the first mobility.

According to one embodiment, the sensing step may further include at least one of a speed measuring unit, an image acquisition unit, a sound acquisition unit, a wheel monitoring unit, and a manipulation apparatus unit, which are included in the first mobility.

According to one embodiment, the speed measuring unit may measure at least one of a speed and a direction of the first mobility, and the determining step may include determining that the predetermined event has occurred to the first mobility, when at least one of the measured speed and the measured direction exceeds a predetermined threshold within a predetermined time range.

According to one embodiment, the image acquisition unit may monitor a distance between the first mobility and an object that is different from the first mobility, and the determining step may include determining that the predetermined event has occurred to the first mobility, when the distance becomes below a predetermined threshold within a predetermined time range.

According to one embodiment, the sound acquisition unit may acquire a sound generated from at least one of the inside and the outside of the first mobility, and the determining step may include determining that the predetermined event has occurred to the first mobility, when a volume of the sound exceeds a predetermined threshold within a predetermined time range.

According to one embodiment, the wheel monitoring unit may monitor at least one level of a temperature and a pressure inside a wheel of the first mobility, and the determining step may include determining that the predetermined event has occurred to the first mobility, when the level exceeds a predetermined threshold within a predetermined time range.

According to one embodiment, the manipulation apparatus unit may monitor a pressure upon at least one of a steering wheel, an accelerator pedal, and a brake of the first mobility, and the determining step may include determining that the predetermined event has occurred to the first mobility, when a magnitude of the pressure exceeds a predetermined threshold within a predetermined time range.

According to one embodiment, the error monitoring method may further include determining whether or not the predetermined event has occurred to the first mobility by applying a predetermined threshold to at least one among the speed measuring unit, the image acquisition unit, the sound acquisition unit, the wheel monitoring unit, and the manipulation apparatus unit. The predetermined threshold is a value set by a user input or a predefined value. A magnitude of the predetermined threshold may be set according to the speed measuring unit, the image acquisition unit, the sound acquisition unit, the wheel monitoring unit, and the manipulation apparatus unit, respectively.

According to one embodiment, the event-related potential (ERP) may include at least one of error-related negativity (ERN) and error positivity (Pe).

According to one embodiment, the event-related potential (ERP) may further include at least one of correct-related negativity (CRN) and correct positivity (Pc).

According to one embodiment, the analysis may compare an amplitude of an event-related potential, which is collected for the predetermined time, and a predetermined threshold.

According to one embodiment, the predetermined threshold may be differently determined according to at least one of a type of the ERP and a passenger from whom the ERP is obtained.

According to one embodiment, when an amplitude of an ERP collected for a predetermined time exceeds the predetermined threshold range, the transmitting step may include transmitting error information of the first mobility to the traffic control server.

In addition, the present disclosure may provide an operating method for a traffic control server, including receiving error information of a first mobility from the first mobility and controlling by determining a degree of responsibility for a first event occurring to the first mobility on the basis of the error information of the first mobility. The first event includes a traffic accident at least related to the first mobility. The error information of the first mobility includes at least one of time information regarding when an event-related potential for at least one passenger in the first mobility occurs, a waveform of the event-related potential, location information of the first mobility, and operational information of the first mobility.

According to one embodiment, the controlling step may include identifying a first event occurring to the first mobility by using error information of the first mobility.

According to one embodiment, the controlling step may include obtaining information related to the first event from an image acquisition unit that is installed within a predetermined range around a location of the first mobility and identifying the first event occurring to the first mobility by using the obtained information and the error information of the first mobility.

According to one embodiment, the receiving step may further include receiving error information of at least one second mobility from the second mobility that is different from the first mobility, and the controlling step may further include identifying a second event occurring to the second mobility by using the error information of the second mobility and selecting a second mobility related to the first event on the basis of the identified second event.

According to one embodiment, the selecting step for a second mobility related to the first event may include selecting a second mobility to which the second event occurs, when the second event is the same as the first event.

According to one embodiment, the controlling step may further include determining a degree of responsibility for the occurrence of the first event between the first mobility and the selected second mobility.

According to one embodiment, the degree of responsibility may be proportional to a peak value of ERP of the first mobility and a peak value of ERP of the second mobility.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIGS. 4A and 4B are views respectively illustrating measurement areas of ERP and Pe in one form of the present disclosure;

Figure 1:
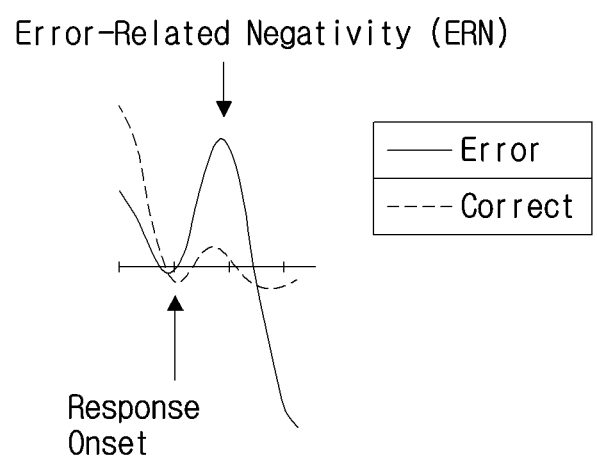
FIG. 1 is a view illustrating a general waveform of ERN in one form of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

The following description is merely exemplary in nature and is not intended to limit the present disclosure, application, or uses. It should be understood that throughout the drawings, corresponding reference numerals indicate like or corresponding parts and features.

Exemplary forms of the present disclosure will be described in detail such that the ordinarily skilled in the art would easily understand and implement an apparatus and a method provided by the present disclosure in conjunction with the accompanying drawings. However, the present disclosure may be embodied in various forms and the scope of the present disclosure should not be construed as being limited to the exemplary forms.

In describing forms of the present disclosure, well-known functions or constructions will not be described in detail when they may obscure the spirit of the present disclosure.

In the present disclosure, it will be understood that when an element is referred to as being "connected to", "coupled to", or "combined with" another element, it can be directly connected or coupled to or combined with the another element or intervening elements may be present therebetween. It will be further understood that the terms "comprises", "includes", "have", etc. when used in the present disclosure specify the presence of stated features, integers, steps, operations, elements, components, and/or combinations thereof but do not preclude the presence or addition of one or more other features, integers, steps, operations, elements, components, and/or combinations thereof.

It will be understood that, although the terms "first", "second", etc. may be used herein to describe various elements, these elements should not be limited by these terms. These terms are only used to distinguish one element from another element and not used to show order or priority among elements. For instance, a first element discussed below could be termed a second element without departing from the teachings of the present disclosure. Similarly, the second element could also be termed as the first element.

In the present disclosure, distinguished elements are termed to clearly describe features of various elements and do not mean that the elements are physically separated from each other. That is, a plurality of distinguished elements may be combined into a single hardware unit or a single software unit, and conversely one element may be implemented by a plurality of hardware units or software units. Accordingly, although not specifically stated, an integrated form of various elements or separated forms of one element may fall within the scope of the present disclosure. Also, the terms, such as 'unit' or 'module', etc., should be understood as a unit that processes at least one function or operation and that may be embodied in a hardware manner (e.g., a processor), a software manner, or a combination of the hardware manner and the software manner.

In the present disclosure, all of the constituent elements described in various forms should not be construed as being essential elements but some of the constituent elements may be optional elements. Accordingly, forms configured by respective subsets of constituent elements in a certain form also may fall within the scope of the present disclosure. In addition, forms configured by adding one or more elements to various elements also may fall within the scope of the present disclosure.

As an electrical activity of neurons constituting a brain, a brain wave signal (or brain signal, brain wave) means a bio signal that directly and indirectly reflects a conscious or nonconscious state of a person. A brain wave signal can be measured in every area of human scalp, and its wavelength has a frequency of mainly 30 Hz or below and a potential difference of scores of microvolts. Depending on brain activity and state, various waveforms may appear. A research on interface control using a brain wave signal according to a person's intention is under way. A brain wave signal may be obtained by using EEG (Electro Encephalo Graphy) using electrical signals caused by brain activities, MEG (Magneto Encephalo Graphy) using magnetic signals occurring with electrical signals, and fMRI (functional Magnetic Resonance Imaging) or fNIRS (Near-Infrared Spectroscopy) using a change of oxygen saturation in the blood. Although fMRI and fNIRS are useful techniques for measuring brain activities, fMRI has a low time-resolution and fNIRS has a low spatial-resolution in general. Due to these limitations, EEG signals are mostly used by virtue of excellent portability and time-resolution.

A brain wave signal changes spatially and over time according to brain activity. As a brain wave signal is usually difficult to analyze and its waveform is not easy to visually analyze, various processing methods are proposed.

For example, according to the number of oscillations (frequency), brain wave signals may be classified based on frequency bands (Power spectrum classification). The classification considers a measured brain wave signal as a linear sum of simple signals at each specific frequency, decomposes the signal into each frequency component and indicates a corresponding amplitude. A brain wave signal at each frequency may be obtained by using pre-processing normally for noise elimination, the Fourier transform into frequency domain, and a band-pass filter (BPF).

More particularly, according to frequency band, brain waves may be classified into delta, theta, alpha, beta and gamma waves. Delta waves are brain waves with a frequency of 3.5 Hz or below and an amplitude of 20~200 µV, mainly appearing in normal deep sleep or newborns. In addition, delta waves may increase as our awareness of the physical world decreases. Generally, theta waves are brain waves with a frequency of 3.5~7 Hz, mainly appearing in emotionally stable states or in sleep.

In addition, theta waves are generated mainly in the parietal cortex and in the occipital cortex and may appear during calm concentration for recollecting a memory or meditating. Generally, alpha waves are brain waves with a frequency of 8~12 Hz, mainly appearing in relaxed and comfortable states. In addition, alpha waves are normally generated in the occipital cortex during rest and may diminish in sleep. Generally, beta waves are brain waves with a frequency of 13~30 Hz, mainly appearing in a state of tension, which is bearable enough, or while a certain level of attention is paid. In addition, beta waves are mainly generated in the frontal cortex and are related to an awakened state or concentrated brain activities, pathological phenomena and medicinal effects. Beta waves may appear in a wide area throughout the brain. In addition, specifically, the beta waves may be divided into SMR waves with a frequency of 13~15 Hz, mid-beta waves with a frequency of 15~18 Hz and high beta waves with a frequency of 20 Hz and above. As beta waves appear to be stronger under stress like anxiety and tension, they are called stress waves. Gamma waves are brain waves that generally have a frequency of 30~50 Hz, mainly appearing in a strongly excited state or during high-level cognitive information processing. In addition, gamma waves may appear in an awaking state of consciousness and during REM sleep and may also be overlapped with beta waves.

Each of the brain wave signals according to frequency band is associated with a specific cognitive function. For example, delta waves are associated with sleep, theta waves are associated with working memory, and alpha waves are associated with attention or inhibition. Thus, the property of a brain wave signal at each frequency band selectively displays a specific cognitive function. In addition, the brain wave signal at each frequency band may show a little different aspect in each measuring part on the surface of head. The cerebral cortex may be divided into frontal cortex, parietal cortex, temporal cortex and occipital cortex. These parts may have a few different roles. For example, the occipital cortex corresponding to the back of head has the primary visual cortex and thus can primarily process visual information. The parietal cortex located near the top of head has the somatosensory cortex and thus can process motor/sensory information. In addition, the frontal cortex can process information related to memory and thinking, and the temporal cortex can process information related to auditory sense and olfactory sense.

Meanwhile, for another example, a brain wave signal may be analyzed by using ERP (Event-Related Potential). ERP is an electrical change in a brain in association with a stimulus from outside or a psychological process inside. ERP means a signal including an electrical activity of the brain, which is caused by a stimulus including specific information (for example, image, voice, sound, command of execution, etc.) after a certain time since the stimulus is presented.

To analyze an ERP, a process of separating a signal from a noise is desired. An averaging method may be mainly used. Particularly, by averaging brain waves measured based on stimulus onset time, it is possible to remove brain waves, which are not related to a stimulus, and to pick out only a related potential, that is, a brain activity commonly associated with stimulus processing.

As ERP has a high time resolution, it is closely related to a research on cognitive function. ERP is an electrical phenomenon that is evoked by an external stimulus or is related to an internal state. According to types of stimuli, ERPs may be classified into auditory sense-related potentials, sight-related potentials, somatic sense-related potentials and olfactory sense-related potentials. According to properties of stimuli, ERPs may be classified into exogenous ERPs and endogenous ERPs. Exogenous ERPs have a waveform determined by an external stimulus, are related to automatic processing, and mainly appear in the initial phase of being given the stimulus. For example, exogenous ERPs are brainstem potentials. On the other hand, endogenous ERPs are determined by an internal cognitive process or a psychological process or state, irrespective of stimuli, and are related to 'controlled processing'. For example, endogenous ERPs are P300, N400, P600, CNV (Contingent Negative Variation), etc.

Names given to ERP peaks normally include a polarity and a latent period, and the peak of each signal has an individual definition and meaning. For example, the positive potential is P, the negative potential is N, and P300 means a positive peak measured about 300 ms after the onset of a stimulus. In addition, 1, 2, 3 or a, b, c and the like are applied according to the order of appearance. For example, P3 means a third positive potential in waveform after the onset of a stimulus.

Hereinafter, various ERPs will be described.

For example, N100 is related to a response to an unpredictable stimulus.

MMN (Mismatch Negativity) may be generated not only by a focused stimulus but also by non-focused stimulus. MMN may be used as an indicator for whether or not a sense memory (echoic memory) operates before initial attention. P300, which will be described below, appears in a process of paying attention and making judgment, while MMN is analyzed as a process occurring in the brain before paying attention.

For another example, N200 (or N2) is mainly generated according to visual and auditory stimuli and is related to short-term memory or long-term memory, which are types of memories after attention, along with P300 described below.

For yet another example, P300 (or P3) mainly reflects attention to a stimulus, stimulus cognition, memory search and alleviation of uncertain feeling and is related to perceptual decision distinguishing stimuli from outside. As the generation of P300 is related to a cognitive function, P300 is generated irrespective of types of presented stimuli. For example, P300 may be generated in auditory stimuli, visual stimuli and somatic stimuli. P300 is widely applied to a research on brain-computer interface.

For yet another example, N400 is related to language processing and is caused when a sentence or an auditory stimulus with a semantic error is presented. In addition, N400 is related to a memory process and may reflect a process of retrieving or searching information from long-term memory.

For yet another example, as an indicator showing reconstruction or recollective process, P600 is related to a process of processing a stimulus more accurately based on information stored in long-term memory.

For yet another example, CNV refers to potentials appearing for 200~300 ms and even for a few seconds in the later phase. It is also called slow potentials (SPs) and is related to expectancy, preparation, mental priming, association, attention and motor activity.

For yet another example, ERN (Error-Related Negativity) or Ne (error negativity) is an event-related potential (ERP) generated by a mistake or an error. It may occur when a subject makes a mistake in a sensorimotor task or a similar task. More particularly, when a subject cognizes a mistake or an error, ERN is generated and its negative peak appears mainly in the frontal and central zones for about 50~150 ms. Especially, it may appear in a situation, where a mistake related to motor response is likely to occur, and may also be used to indicate a negative self-judgment.

Hereinafter, the major features of ERN will be described in more detail.

FIG. 1 is a view illustrating a general waveform of ERN according to one form of the present disclosure.

Referring to FIG. 1, negative potential values are depicted above the horizontal axis, and positive potential values are depicted below the horizontal axis. In addition, it can be confirmed that an ERP with a negative peak value is generated within a predetermined time range after a response onset for an arbitrary motion. Herein, the response may mean a case where a mistake or an error is made (Error Response). In addition, the predetermined time range may be about 50~150 ms. Alternatively, the predetermined time range may be about 0~100 ms. Meanwhile, in the case of a correct response, an ERP is generated which has a relatively smaller negative peak than ERN.

As an ERP of initial negativity, ERN is time-locked until a response error occurs. In addition, ERN is known to reflect the reinforcement activity of a dopaminergic system related to behavioral monitoring. ERN includes the fronto-striatal loop including the rostral cingulate zone. Meanwhile, dopamine is associated with the reward system of brain that usually forms a specific behavior and motivates a person thereby providing pleasure and reinforced feelings. When a behavior obtaining an appropriate reward is repeated, it is learned as a habit. In addition, more dopamine is released through emotional learning, and a new behavior is attempted due to the release of dopamine. Thus, reward-driven learning is called reinforcement learning.

In addition, ERN may be generated in 0~100 ms after the onset of an erroneous response that is caused during an interference task (for example, Go-noGo task, Stroop task, Flanker task, and Simon task) through the frontal cortex lead.

In addition, together with CRN described below, ERN is known to reflect a general behavior monitoring system that can distinguish a right behavior and a wrong behavior.

In addition, the fact that ERN reaches a maximum amplitude at the frontal cortex electrode is known to reflect that an intracerebral generator is located in the rostral cingulate zone or the dorsal anterior cingulate cortex (dACC) zone.

In addition, ERN may show a change of amplitude according to a negative emotional state.

In addition, ERN may be reported even in a situation where behavioral monitoring is performed based on external evaluation feedback processing unlike internal motor expression, and may be classified as FRN described below.

In addition, ERN may be generated not only when having cognized a mistake or an error but also before cognizing the mistake or the error.

In addition, ERN may be generated not only as a response to his/her own mistake or error but also as a response to a mistake or error of others.

In addition, ERN may be generated not only as a response to a mistake or an error but also as a response to anxiety or stress for a predetermined performance task or object.

In addition, as a larger peak value of ERN is obtained, it may be considered as reflecting a more serious mistake or error.

Meanwhile, for yet another example, being an event-related potential (ERP) that is generated after ERN, Pe (Error Positivity) is an ERP with a positive value, which is generated mainly at the frontal cortex electrode in about 150~300 ms after a mistake or an error. Pe is known as a reaction that realizes a mistake or an error and pays more attention. In other words, Pe is related to an indicator of a conscious error information processing process after error detection. ERN and Pe are known as ERPs related to error monitoring.

Hereinafter, the major features of Pe will be described in more detail.

Figure 2:
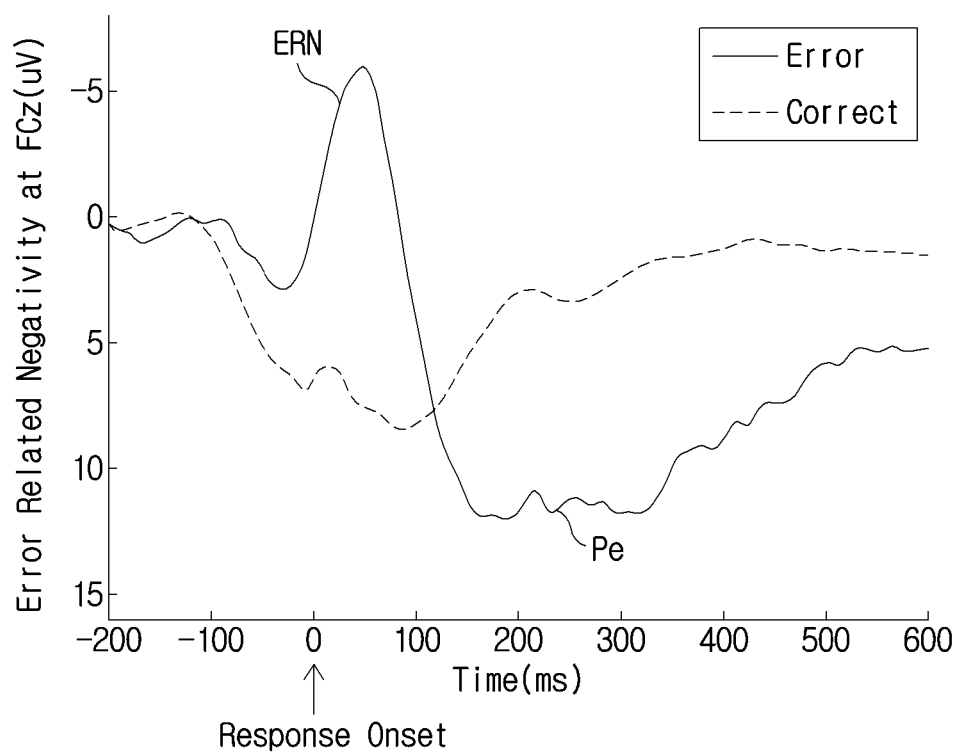
FIG. 2 is a view illustrating general waveforms of ERN and Pe according to one form of the present disclosure.

FIG. 2 is a view illustrating general waveforms of ERN and Pe according to another form of the present disclosure.

Referring to FIG. 2, negative potential values are depicted above positive potential values. In addition, it can be confirmed that an ERP with a negative peak value, that is, an ERN is generated within a first predetermined time range after a response onset for an arbitrary motion. Herein, the response may mean a case where a mistake or an error is made (Error Response). In addition, the first predetermined time range may be about 50~150 ms. Alternatively, the first predetermined time range may be about 0~200 ms.

In addition, it can be confirmed that an ERP with a positive peak value, that is, a Pe is generated within a second predetermined time range after the onset of the ERN. In addition, the second predetermined time range may be about 150~300 ms after an error onset. Alternatively, the second predetermined time range may mean about 200~400 ms.

Figure 3:
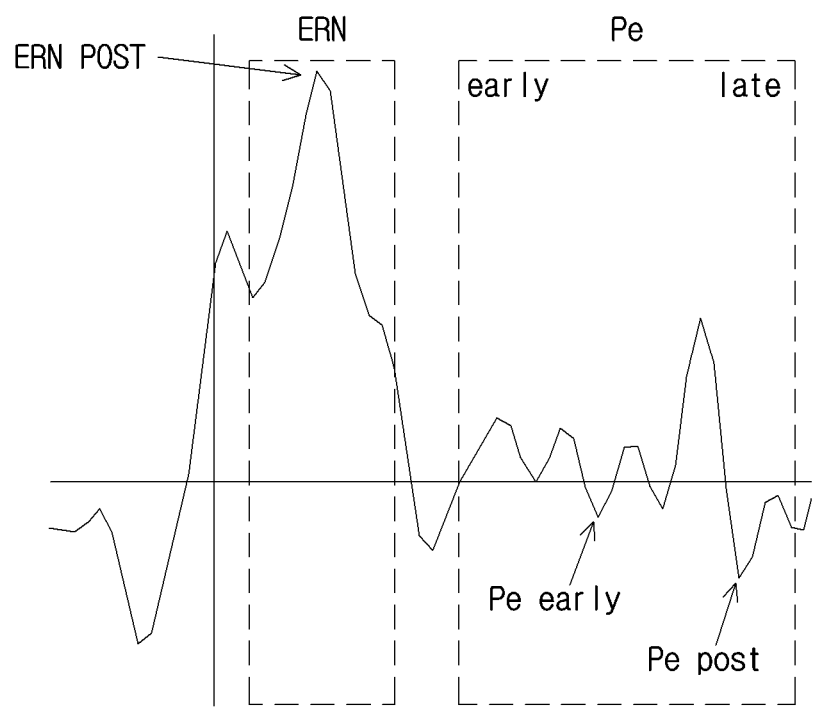
FIG. 3 is a view illustrating a deflection characteristic of Pe according to another form of the present disclosure.

FIG. 3 is a view illustrating a deflection characteristic of Pe in one form of the present disclosure.

Referring to FIG. 3, like P3, Pe has a wide deflection characteristic, and the plexus generator includes not only the areas of posterior cingulate cortex and insula cortex but also more anterior cingulate cortex.

In addition, Pe may reflect an emotional evaluation of an error and an attention to a stimulus like P300. In addition, ERN indicates a conflict between a right response and a wrong response, and Pe is known to be a response that realizes a mistake and pays more attention. In other words, ERN may be generated in a process of detecting a stimulus, and Pe may be generated depending on attention in a process of processing a stimulus. When ERN and/or Pe have relatively large values respectively, it is known that the values are related to an adaptive behavior intended to respond more slowly and more accurately after a mistake.

FIGS. 4A and 4B are views illustrating measurement areas of ERP and Pe according to one form of the present disclosure.

ERN and Pe are known as ERPs related to error monitoring. Regarding the measurement areas of ERN and Pe, a largest negative value and a largest positive value may normally be measured in the central area. However, there may be a little difference according to measurement conditions. For example, FIG. 4A is the main area where ERN is measured, and the largest negative value of ERN may normally be measured in the midline frontal or central zone (that is, FCZ). In addition, FIG. 4B is the main area where Pe is measured, and a large positive value of Pe may normally be measured in a posterior midline zone as compared to ERN.

Meanwhile, for yet another example, FRN (Feedback-Related Negativity) is an event-related potential (ERP) that is related to error detection obtained based on external evaluation feedback. ERN and/or Pe detect an error based on an internal monitoring process. However, in the case of FRN, when being obtained based on external evaluation feedback, it may operate similarly to the process of ERN.

In addition, FRN and ERN may share many electrophysiological properties. For example, FRN has a negative peak value at the frontal cortex electrode in about 250~300 ms after the onset of a negative feedback and may be generated in the dorsal anterior cingulate cortex (dACC) zone like ERN.

In addition, like ERN, FRN may reflect an activity of reinforcement learning by a dopaminergic system. In addition, FRN normally has a larger negative value than a positive feedback and may have a larger value for an unforeseen case than for a predictable result.

Figure 5:
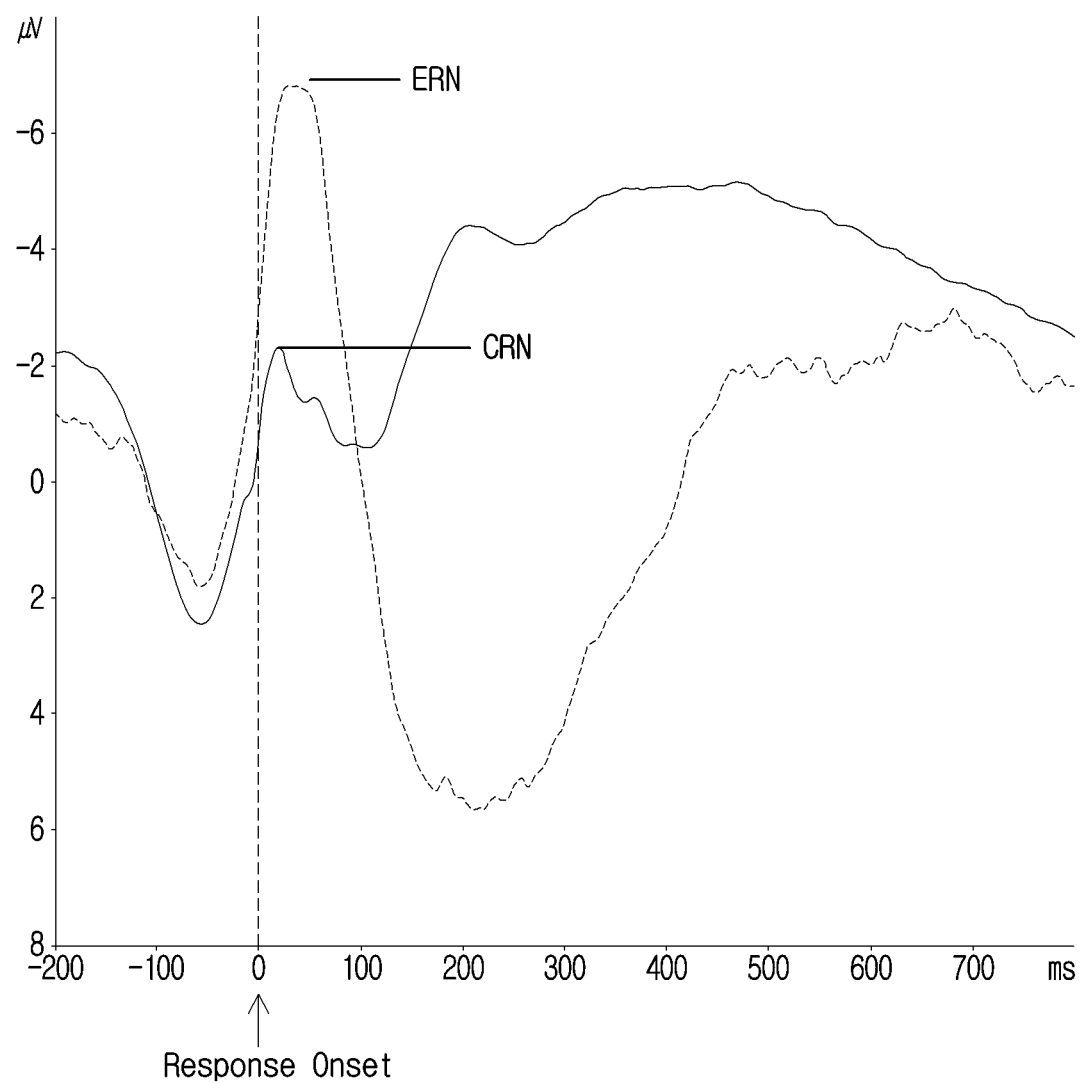
FIG. 5 is a view illustrating general waveforms of ERN and CRN according to one form of the present disclosure.

For yet another example, CRN (Correct-Related Negativity) is an ERP generated by a correct trial and is a negative value that is smaller than ERN. Like ERN, CRN may be generated in the initial latent period (for example, 0~100 ms). FIG. 5 is a view illustrating general waveforms of ERN and CRN in one form of the present disclosure.

For yet another example, Pc (Correct Positivity) is an event-related potential generated following CRN. It is an event-related potential generated in about 150~300 ms after the onset of correct response. The relation between CRN and Pc may be similar to the relation between ERN and Pe.

Meanwhile, ERPs may be classified into stimulus-locked ERPs and response-locked ERPs. The stimulus-locked ERPs and the response-locked ERPs may be divided according to criteria like evoking cause of ERP and response time. For example, an ERP evoked from a moment when a word or a picture is presented to a user from outside may be called a stimulus-locked ERP. In addition, for example, an ERP evoked from a moment when a user speaks or pushed a button may be called a response-locked ERP. Accordingly, based on the above-described criterion, in general, stimulus-locked ERPs are N100, N200, P2, P3, etc., and response-locked ERPs are ERN, Pe, CRN, Pc, FRN, etc.

Meanwhile, brain waves may be classified according to manifesting motives. Brain waves may be classified into spontaneous brain waves (spontaneous potentials) manifested by a user's will and evoked brain waves (evoked potentials) that are naturally manifested according to external stimuli irrespective of the user's will. Spontaneous brain waves may be manifested when a user moves on his/her own or imagines a movement, while evoked brain waves may be manifested by visual, auditory, olfactory and tactile stimuli, for example.

Meanwhile, brain wave signals may be measured in accordance with the International 10-20 system. The International 10-20 system determines measurement points of brain wave signals on the basis of the relationship between the location of an electrode and the cerebral cortex areas.

Figure 6:
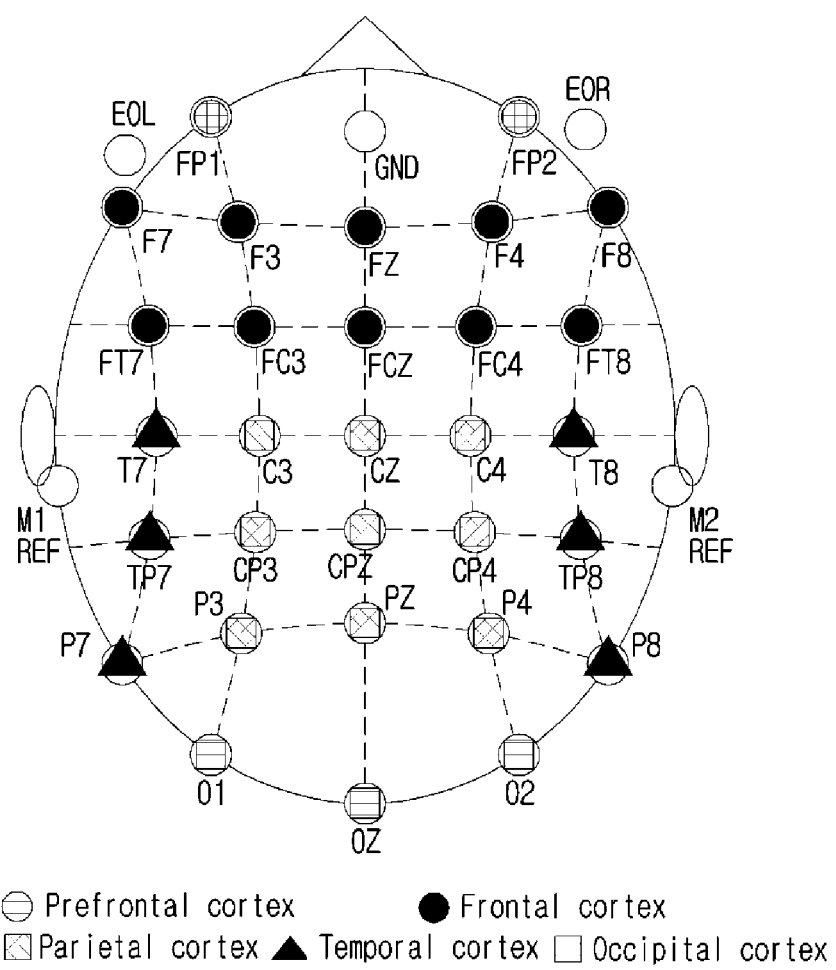
FIG. 6 is a view illustrating EEG measurement channels corresponding to cerebral cortex areas in one form of the present disclosure.

FIG. 6 is a view illustrating EEG measurement channels corresponding to the cerebral cortex areas according to one form of the present disclosure.

Referring to FIG. 6, brain areas (Prefrontal cortex FP1, FP2; Frontal cortex F3, F4, F7, F8, FZ, FC3, FC4, FT7, FT8, FCZ; Parietal cortex C3, C4, CZ, CP3, CP4, CPZ, P3, P4, PZ; Temporal cortex T7, T8, TP7, TP8, P7, P8; Occipital cortex O1, O2, OZ) correspond to 32 brain wave measurement channels. For each of the channels, data may be obtained and analysis may be performed for each cerebral cortex area by using the data.

Figure 7:
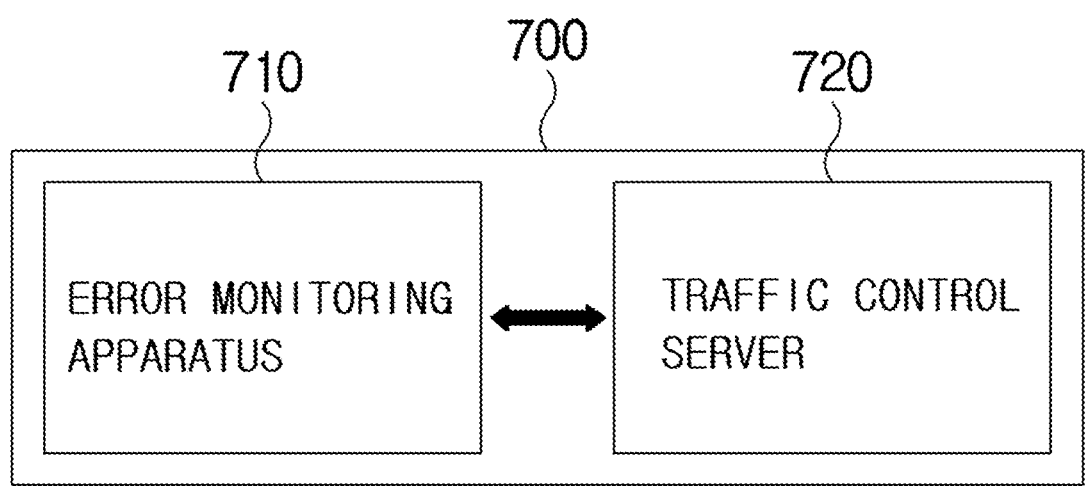
FIG. 7 is a block diagram illustrating a configuration of a traffic accident analysis system using error monitoring in one form of the present disclosure.

FIG. 7 is a block diagram illustrating a configuration of a traffic accident analysis system using error monitoring according to an embodiment of the present disclosure.

Traffic accidents are typically caused by human factors, vehicle factors and road environment factors. The majority of traffic accidents are caused by human factors. Particularly, human factors include a driver's mistake, carelessness, poor driving, sleepiness, drunkenness, and disobedience to traffic rules, and vehicle factors include defects in design and functions and negligence of maintenance. In addition, road environment factors include road designs, negligence of maintenance, construction, weather, visibility and lighting.

A response-locked ERP occurs when a mistake or an error is perceived. In addition, a response-locked ERP may be generated not only as a response to his/her own mistake or error but also as a response to a mistake or error of others. In addition, a response-locked ERP may be generated as a response to anxiety or stress for a predetermined performance task or object. Herein, a response-locked ERP may include ERN, Pe, CRN, Pc and FRN.

Meanwhile, a drastic change in a passenger's or an observer's brain wave signal may be observed within a predetermined time range before and after a traffic accident. In other words, as a brain wave signal is a bio signal that directly and indirectly reflects a conscious or nonconscious state of a person, a feeling caused by an impact of a traffic accident on a mobility or a passenger's or an observer's anxiety, stress or feeling for driving mistake or error before and after a traffic accident may cause a drastic change in a brain wave signal of the passenger or the observer. Herein, a driver's act of violating a traffic regulation or causing a traffic accident may be considered as a type of mistake or error.

Accordingly, when an observer's brain wave signal related to a traffic accident is analyzed within a predetermined time range before and after the traffic accident, a response-locked ERP generated as a response to anxiety, stress, mistake and error may be obtained.

Here, the observer related to the traffic accident may be a passenger of a mobility that is a direct object of the traffic accident. In addition, a passenger of a mobility and/or an observer who observe the corresponding traffic accident or indirectly influence or are influenced by the traffic accident may be included.

In addition, the mobility may encompass the meanings of vehicle, moving/transport apparatus and the like.

Meanwhile, once a traffic accident occurs, a corresponding mobility normally undergoes a predetermined impact. Thus, when the occurrence of a predetermined impact is detected, it may be determined whether or not a traffic accident has occurred to the corresponding mobility. In addition, the occurrence of the predetermined impact may be detected by using various sensing apparatuses included in the corresponding mobility.

In addition, as a peak value of ERP that is generally obtained is larger, a response-locked ERP may be considered as reflecting a more serious mistake or error. Accordingly, an observer who is more responsible for a traffic accident or gives a greater motivation to the traffic accident may be selected by comparing amplitudes of ERPs between a plural of observers related to the traffic accident.

For example, when a speeding vehicle collides with another vehicle, a driver committing speeding may be expected to have recognized a greater possibility of traffic accident in comparison with a driver of the another vehicle being hit.

For another example, when a speeding vehicle collides with another vehicle, a driver committing speeding may be expected to have perceived the occurrence of the traffic accident at an earlier time in comparison with a driver of the another vehicle being hit.

For yet another example, a brain wave signal of a driver under the influence of alcohol or sleepiness may better reflect the driver's mental states like anxiety and stress in comparison with a brain wave signal of another driver not under such influence. Furthermore, when a feature of a response-locked ERP is considered, a driver's brain wave signal may reflect his/her mental state like anxiety and stress not only in a situation which the driver is aware of but also in other situations which the driver is not aware of.

A traffic accident analysis system of the present disclosure may determine a primary responsibility for a traffic accident between mobilities by using a response-locked ERP obtained from an observer witnessing a mobility to which the traffic accident occurs. In addition, a traffic analysis system may express a primary responsibility for a traffic accident between mobilities as a specific figure.

Referring to FIG. 7, a traffic accident analysis system 700 may include an error monitoring apparatus 710 or a traffic control server 720 or both. It should be noted, however, that only some of the components necessary for explaining the present embodiment are illustrated and the components included in the traffic accident analysis system 700 are not limited to the embodiment. For example, two or more constituent units may be implemented in one constituent unit, and an operation performed in one constituent unit may be divided and executed in two or more constituent units. Also, some constituent units may be omitted or additional constituent units may be added.

The error monitoring apparatus 710 of the present disclosure may transmit error information of a mobility to a server.

For example, the error monitoring apparatus 710 may determine whether or not a predetermined event has occurred to a first mobility. In addition, the error monitoring apparatus 710 may collect an ERP for at least one passenger in a first mobility for a predetermined time. In addition, the error monitoring apparatus 710 may analyze an ERP that is collected for a predetermined time. In addition, based on a result of the analysis, the error monitoring apparatus 710 may transmit error information of the first mobility to the traffic control server 720.

Herein, a predetermined event may mean a traffic accident related to a first mobility. The first mobility may be a mobility that is the main cause of the traffic accident. Alternatively, the first mobility may include a mobility that is not the main cause of the traffic accident or a mobility that is related to the traffic accident but not an object of the traffic accident.

In this case, error information of the first mobility may include time information regarding when an ERP occurs for at least one passenger in the first mobility, a waveform of the ERP, and location information and/or operational information of the first mobility.

Figure 9:
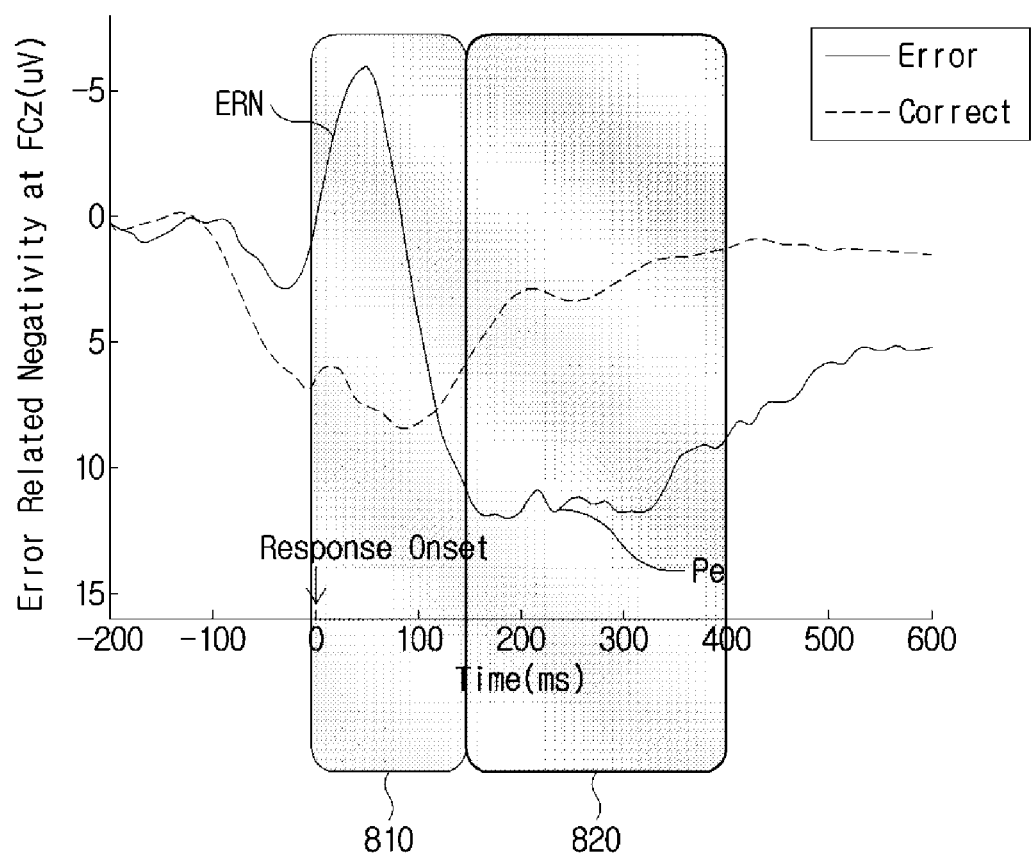
FIG. 9 is a view illustrating a measurement time range, when a target ERP is ERN and Pe, in one form of the present disclosure.
Figure 10:
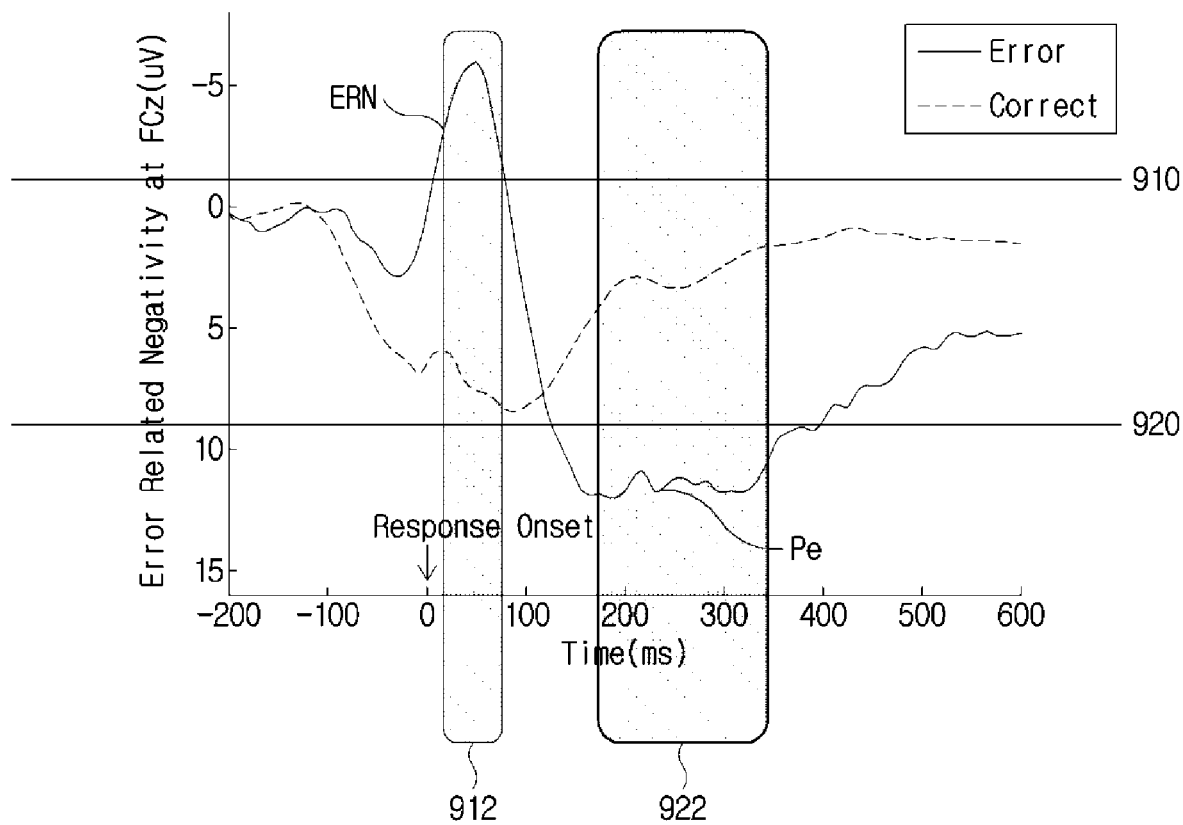
FIG. 10 is a view illustrating a process of comparing a target ERP and a predetermined threshold, when the target ERP is ERN and Pe respectively, in one form of the present disclosure.

A further detailed operation of the error monitoring apparatus 710 are described in FIG. 9 and FIG. 10 below.

The traffic control server of the present disclosure may determine a mobility with a primary responsibility for a corresponding traffic accident by using error information of a mobility received from the error monitoring apparatus 710.

For example, the traffic control server 720 may identify a predetermined event occurring to a mobility by using error information of the mobility received from the error monitoring apparatus 710. In addition, the traffic control server 720 may select mobilities related to the predetermined event thus identified among a plural of mobilities of which error information is received. For example, among a plural of mobilities, mobilities may be selected for which the predetermined event is commonly identified. In addition, among a plural of mobilities, mobilities may be selected which commonly have the identified traffic accident event. Accordingly, mobilities related to a same traffic accident may be selected. In addition, the traffic control server 720 may express a degree of responsibility for a corresponding traffic accident between the selected mobilities by a numerical value. In addition, the traffic control server 720 may determine a mobility with a primary responsibility for the corresponding traffic accident on the basis of the numerical value.

Herein, the traffic control server 720 may mean a server that is capable of identifying and analyzing a process before and after a traffic accident between mobilities by collecting and analyzing data given by mobilities. For example, the traffic control server 720 may mean a traffic control center server of a district police station.

A further detailed operation of the traffic control server 720 is described in FIG. 11 below.

Figure 8:
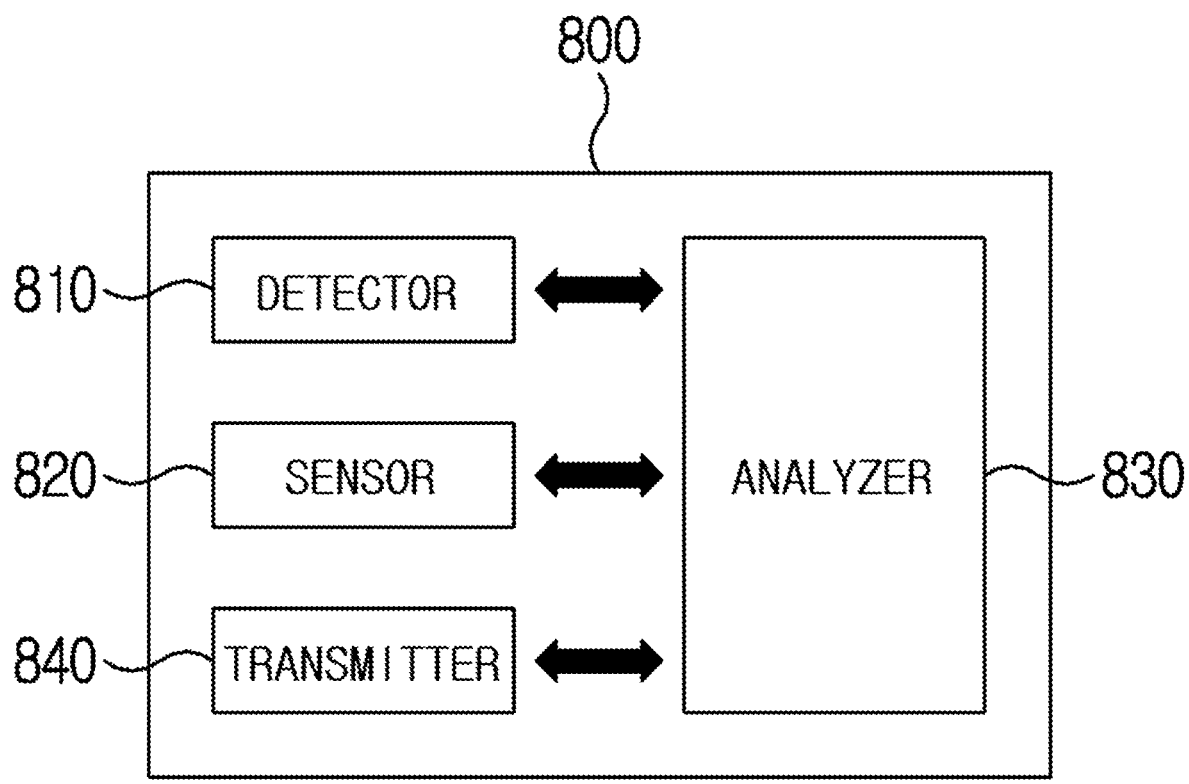
FIG. 8 is a block diagram illustrating a configuration of an error monitoring apparatus in one form of the present disclosure.

FIG. 8 is a block diagram illustrating a configuration of an error monitoring apparatus according to an embodiment of the present disclosure.

Referring to FIG. 8, an error monitoring apparatus 800 may include a detecting unit 810, a sensing unit 820, an analysis unit 830 and/or a transmission unit 840. It should be noted, however, that only some of the components necessary for explaining the present embodiment are illustrated and the components included in the error monitoring apparatus 800 are not limited to the embodiment. For example, two or more constituent units may be implemented in one constituent unit, and an operation performed in one constituent unit may be divided and executed in two or more constituent units. Also, some constituent units may be omitted or additional constituent units may be added.

Meanwhile, the error monitoring apparatus 800 of FIG. 8 may be an embodiment of the error monitoring apparatus 710 of FIG. 7.

The error monitoring apparatus 800 of the present disclosure may determine whether or not a predetermined event has occurred to a first mobility. In addition, the detecting unit 810 may perform the operation.

Herein, a predetermined event may mean a traffic accident related to a first mobility. The first mobility may be a mobility that is the main cause of the traffic accident. Alternatively, the first mobility may include a mobility that is not the main cause of the traffic accident or a mobility that is related to the traffic accident but not an object of the traffic accident.

The error monitoring apparatus 800 of the present disclosure may determine whether or not a predetermined event has occurred to a first mobility by using at least one sensing apparatus of the first mobility. In addition, the sensing unit 820 may include the sensing apparatus.

Once a traffic accident occurs, a corresponding mobility normally undergoes a predetermined impact. Thus, when the occurrence of a predetermined impact is detected, it may be determined whether or not a traffic accident has occurred to the corresponding mobility. In addition, the occurrence of the predetermined impact may be detected by using various sensing apparatuses included in the corresponding mobility.

Here, the sensing apparatus may include a speed measuring apparatus, an image acquisition apparatus, a wheel monitoring apparatus, and a manipulation apparatus. The manipulation apparatus may monitor operations of a steering wheel/an accelerator pedal/a brake.

For example, the error monitoring apparatus 800 may determine that a predetermined event has occurred to a first mobility, when a speed or direction of the first mobility exceeds a predetermined threshold within a predetermined time range.

For another example, the error monitoring apparatus 800 may determine that a predetermined event has occurred to a first mobility, when a volume of sound generated inside or outside the first mobility exceeds a predetermined threshold within a predetermined time range.

For yet another example, the error monitoring apparatus 800 may determine that a predetermined event has occurred to a first mobility, when a distance between the first mobility and another mobility becomes below a predetermined threshold within a predetermined time range.

For yet another example, the error monitoring apparatus 800 may determine that a predetermined event has occurred to a first mobility, when an internal temperature and/or an internal pressure of a wheel of the first mobility exceeds a predetermined threshold within a predetermined time range.

For yet another example, the error monitoring apparatus 800 may determine that a predetermined event has occurred to a first mobility, when a magnitude of a force or a pressure upon a steering wheel, an accelerator pedal and a brake of a first mobility exceeds a predetermined threshold within a predetermined time range.

The predetermined time range may be input by a user or a preset value and vary according to each sensing apparatus.

The predetermined threshold may be input by a user or a preset value, and the magnitude and/or unit of the threshold may vary according to each sensing apparatus.

The error monitoring apparatus 800 may collect an ERP for at least one passenger in a mobility for a predetermined time. In addition, the sensing unit 820 may perform the operation.

Herein, the ERP may mean a response-locked ERP. In addition, the response-locked ERP may include ERN, Pe, CRN, Pc and FRN. In addition, apart from the ERN, Pe, CRN, Pc and FRN, other ERPs obtained after a response occurs (that is, response onset) may be included. In addition, the response-locked ERP may include a plural of ERPs.

In addition, herein, collecting the ERP for a predetermined time may include a process of measuring a brain wave signal of at least one passenger in a mobility and detecting an ERP from the measured brain wave signal.

As described in FIGS. 1 to 6, ERN, Pe, CRN, Pc and/or FRN may be generated as responses to wrong behaviors like an error or a mistake or responses to right behaviors. Accordingly, if the ERP is used, it is possible to determine whether or not a corresponding passenger has performed a wrong behavior. Also, based on the determination, a mobility may be controlled to suit a purpose.

For example, when a driver has to make a right turn but makes a left turn or when a driver has to make a left turn but continues straight, ERN and/or Pe may be generated.

For another example, while driving according to a guide of a navigation system, if a driver fails to perform a movement according to the guide, ERN and/or Pe may be generated.

For yet another example, when a driver is in traffic, takes a course for the first time or undergoes a tense and stressful situation on road, ERN and/or Pe may be generated.

For yet another example, ERN and/or Pe may be generated for a feeling caused by an impact of a traffic accident on a mobility or for an anxiety, a stress, and a driving mistake or error felt by a passenger or an observer before and after a traffic accident.

For yet another example, when a driver violates a traffic rule or does something causing a traffic accident, ERN and/or Pe may be generated.

In addition, the predetermined time may mean about 0~400 ms after the onset of a specific response. In addition, the predetermined time may include a time range where the above-described response-locked ERP can be obtained. In addition, the predetermined time may vary according to the type of a response-locked ERP and may have a plural of time ranges. For example, a first time range may be given to obtain a first ERP, and a second time range may be given to obtain a second ERP.

For example, when a first ERP is ERN and a second ERP is Pe, a first time range may be about 0~150 ms that is the main measurement section of ERN, and a second time range may be about 150~400 ms that is the main measurement section of Pe. FIG. 9 is a view illustrating a measurement time range, when a target ERP is ERN and Pe, according to an embodiment of the present disclosure. Referring to FIG. 8, ERN may be obtained in a first time range 910, and Pe may be obtained in a second time range 920.

For another example, when a first ERP is ERN and a second ERP is CRN, a first time range may be about 0~200 ms that is the main measurement section of ERN, and a second time range may be about 0~200 ms that is the main measurement section of CRN.

In addition, the passenger may include not only a driver but also another passenger in a mobility.

When the error monitoring apparatus 800 of the present disclosure determines that a predetermined event has occurred to a first mobility, an ERP collected for a predetermined time may be analyzed. In addition, the analysis unit 830 may perform the operation.

Herein, the analysis may include a process of comparing the amplitude of the ERP, which is collected for the predetermined time, and a predetermined threshold.

Meanwhile, the threshold may be a preset value or a value input by a user. In addition, the threshold may have a different amplitude for each passenger from whom an ERP is collected. For example, it may be a value reflecting the brain wave signal characteristic of each passenger. In order to reflect the analysis result of the brain wave signal characteristic, a predetermined learning process may be performed in advance for response-locked ERP characteristics displayed in a passenger's brain wave signal. In addition, the threshold may vary according to the type of ERP and may have a plural of thresholds. FIG. 10 is a view illustrating a process of comparing a target ERP and a predetermined threshold, when the target ERP is ERN and Pe respectively, according to an embodiment of the present disclosure. Referring to FIG. 10, in the case of ERN, its amplitude may be compared with a first threshold 1010. In the case of Pe, its amplitude may be compared with a second threshold 1020.

In addition, the analysis may include a process of judging whether or not the amplitude of the ERP is equal to or greater than a predetermined threshold (that is, exceeds a predetermined threshold range) during a predetermined time interval. Referring to FIG. 10, in the case of ERN, the amplitude of ERN may be compared with a first threshold 1010 to determine whether or not the amplitude of ERN is equal to or greater than the first threshold 1010 during a third time range 1012. In the case of Pe, the amplitude of Pe may be compared with a second threshold 1020 to determine whether or not the amplitude of Pe is equal to or smaller than the second threshold 1020 during a fourth time range 1022.

In addition, the analysis may be performed by using a brain wave signal template of each passenger. Herein, a brain wave signal template may mean a brain wave signal in a time domain, which is obtained beforehand within a predetermined time range after a response onset for an arbitrary movement. The response may include an error, a mistake, a correct response and the like. The ready-made brain wave signal template may be scaled in the analysis process. In other words, the amplitude of a brain wave signal graph may be increased or decreased at a predetermined rate. For example, the analysis may be performed by comparing an amplitude-time graph waveform of a single ERP and/or a plural of ERPs obtained for a predetermined time with the brain wave signal template that is determined beforehand.

Meanwhile, the analysis may be preceded by a process of cognizing the onset of an ERP by using a time when a characteristic of a brain wave signal appears and/or using a pattern of a brain wave signal. In addition, the analysis may include a process of extracting an ERP.

In addition, an ERP used for the analysis may be a statistical value of ERP collected for a predetermined time. For example, the statistical value may mean an average value, a weighted average value, a maximum value, or a minimum value.

Based on an analysis result of the analysis unit 830, the error monitoring apparatus 800 of the present disclosure may transmit error information of a first mobility to a traffic control server. In addition, the transmission unit 840 may perform the operation.

Here, the error information of a first mobility may include time information regarding when an ERP occurs, a waveform of the ERP, and location information and/or operational information of the first mobility.

Here, the ERP may mean an event-related potential for at least one passenger in the first mobility.

Time information regarding the ERP onset may mean the time of a response onset for the ERP. In other words, referring to FIG. 10, it may mean the response onset time. For example, when an ERP is an ERN, since the main measurement section of ERN is about 0~150 ms after a response onset, the time information regarding the ERP onset may be obtained by subtracting about 0~150 ms from a measurement time point of ERN.

Alternatively, time information regarding the ERP onset may be a measurement time point of a corresponding ERP.

In addition, the location information of the first mobility may mean a location of the first mobility at the measurement time point of the ERP. Meanwhile, a location of a first mobility may be obtained by using GPS and other various types of position recognition systems. Alternatively, a location of a first mobility may be obtained by using a travel direction and an effective velocity of the first mobility, a road slope, etc.

In addition, operational information of a first mobility may mean an operation of a first mobility causing the ERP. For example, it may include a first mobility's crossing over a centerline, speeding and violating a traffic signal or other rules and a first mobility's collision with a second mobility.

Meanwhile, the operational information of a first mobility may be obtained from an image acquisition apparatus like a camera included in the first mobility.

Figure 11:
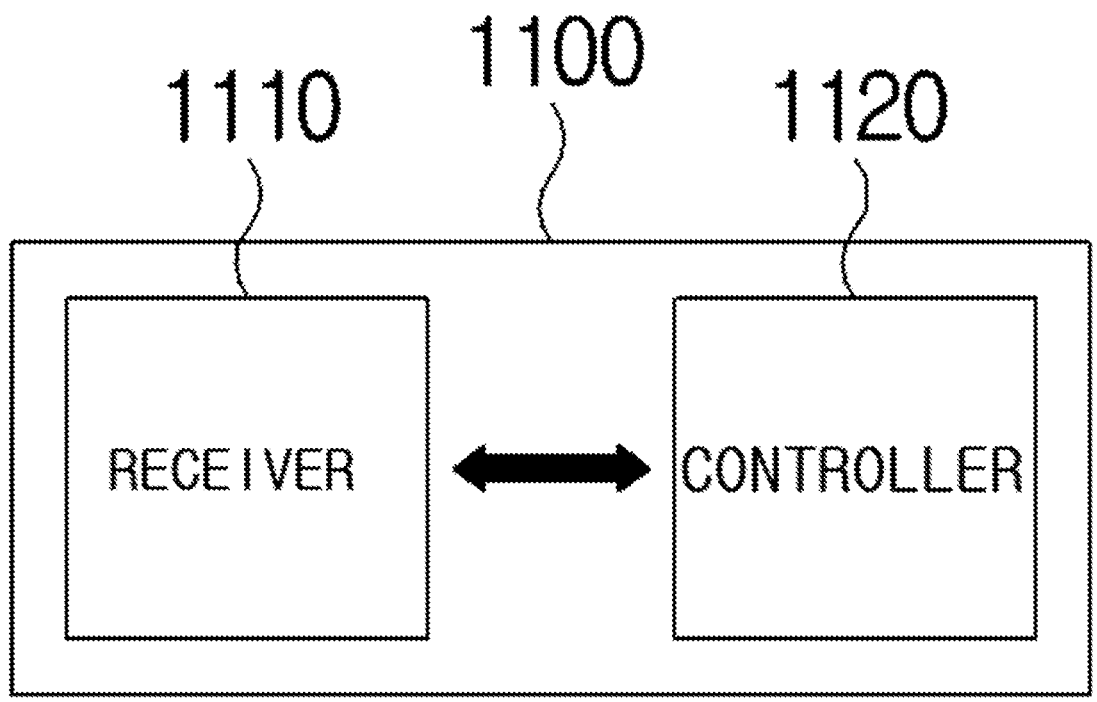
FIG. 11 is a block diagram illustrating a configuration of a traffic control server in one form of the present disclosure.

FIG. 11 is a block diagram illustrating a configuration of a traffic control server according to an embodiment of the present disclosure.

Referring to FIG. 11, a traffic control server 1100 may include a receiver 1110 and/or a controller 1120. It should be noted, however, that only some of the components necessary for explaining the present embodiment are illustrated and the components included in the traffic control server 1100 are not limited to the embodiment. For example, two or more constituent units may be implemented in one constituent unit, and an operation performed in one constituent unit may be divided and executed in two or more constituent units. Also, some constituent units may be omitted or additional constituent units may be added.

Meanwhile, the traffic control server 1100 of FIG. 11 may be an embodiment of the traffic control server 720 of FIG. 7.

The traffic control server 1100 of the present disclosure may receive error information of a first mobility from the first mobility. In addition, the receiver 1110 may perform the operation.

Herein, error information of the first mobility may include time information regarding when an ERP occurs for at least one passenger in the first mobility, a waveform of the ERP, and location information and operational information of the first mobility.

The traffic control server 1100 of the present disclosure may determine a degree of responsibility for a first event occurring to a first mobility on the basis of error information of the first mobility. Here, the controller 1120 may perform the operation.

More particularly, the traffic control server 1100 may identify a first event occurring to a first mobility by using error information of the first mobility.

Herein, identifying a first event occurring to a first mobility may mean identifying a traffic accident situation related to the first mobility.

For example, the traffic control server 1100 may identify a location and time where a traffic accident occurs by using location information of a first mobility, time information regarding the onset of an ERP, etc.

For another example, the traffic control server 1100 may identify a traffic accident occurring to a first mobility by examining traffic accidents within a predetermined time range from when an event-related potential is generated through a closed-circuit television (CCTV) system located within a predetermined range from the location of the first mobility.

For yet another example, the traffic control server 1100 may obtain image and sound information from an image acquisition apparatus like CCTV installed within a predetermined range from the location of a first mobility. In addition, the traffic control server 1100 may determine a degree of responsibility for a first event occurring to a first mobility by using the obtained information and/or error information of the first mobility.

In addition, the traffic control server 1100 may further receive error information of at least one second mobility from the second mobility that is different from a first mobility. In addition, the receiver 1110 may perform the operation.

In addition, the traffic control server 1100 may identify a second event occurring to a second mobility by using error information of the second mobility.

Herein, a second event may mean a traffic accident related to a second mobility. The second mobility may be a mobility that is the main cause of the traffic accident. Alternatively, the second mobility may include a mobility that is not the main cause of the traffic accident or a mobility that is related to the traffic accident but not an object of the traffic accident.

In addition, the traffic control server 1100 may select a second mobility having a second event that is identical with the first event. Herein, identifying a second event occurring to a second mobility may mean identifying a traffic accident situation related to the second mobility. Mobilities related to a same event may be selected by comparing a first event occurring to a first mobility and a second event occurring to a second mobility.

In addition, the traffic control server 1100 may determine a degree of responsibility for the occurrence of a first event between a first mobility and a selected second mobility. Here, the controller 1120 may perform the operation.

Herein, determining a degree of responsibility for the occurrence of a first event may mean determining a fault ratio indicating how much a first mobility and a second mobility are responsible for a corresponding traffic accident. Here, the degree of responsibility may be expressed as a numerical value.

For example, the degree of responsibility may be proportional to a peak value of ERP of a first mobility and a peak value of ERP of a second mobility.

For another example, the degree of responsibility may be determined based on a time point when an ERP of a first mobility and an ERP of a second mobility are displayed.

Figure 12:
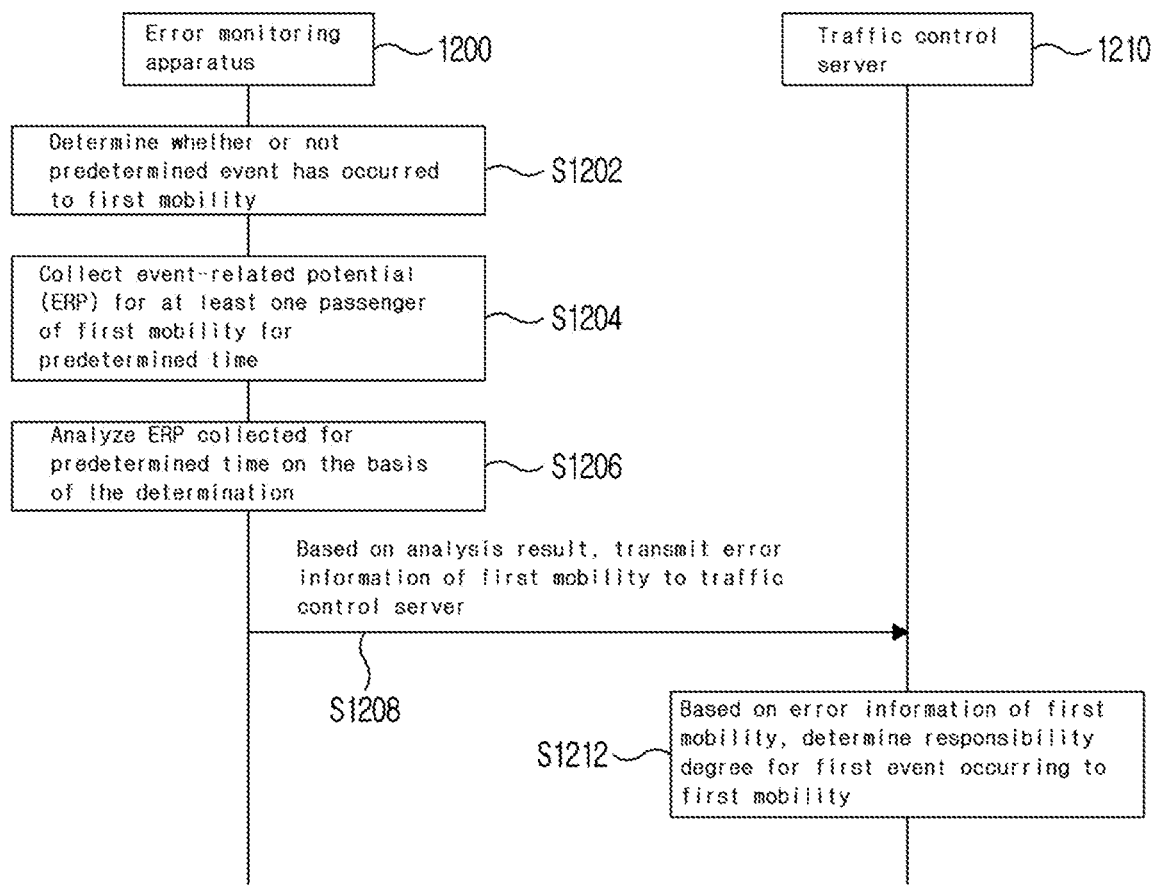
FIG. 12 is a flowchart illustrating an operating method of a traffic accident analysis system using error monitoring in one form of the present disclosure.

FIG. 12 is a flowchart illustrating an operating method of a traffic accident analysis system using error monitoring according to an embodiment of the present disclosure.

A traffic accident analysis system of the present disclosure may include an error monitoring apparatus 1200 transmitting error information of a mobility and/or a traffic control server 1210 that determines a degree of responsibility for the occurrence of a predetermined event between mobilities by using error information of the mobilities.

Referring to FIG. 12, the error monitoring apparatus 1200 may determine whether or not a predetermined event has occurred to a first mobility (S1202).

In addition, the error monitoring apparatus 1200 may collect an ERP for at least one passenger in a first mobility for a predetermined time (S1204).

In addition, the error monitoring apparatus 1200 may analyze an ERP that is collected for a predetermined time (S1206).

Here, the ERP may include at least one of error-related negativity (ERN) and error positivity (Pe). In addition, the ERP may further include at least one of correct-related negativity (CRN) and correct positivity (Pc).

In addition, herein, collecting the ERP for a predetermined time may include a process of measuring a brain wave signal of at least one passenger in a mobility and detecting an ERP from the measured brain wave signal.

In addition, based on an analysis result of the step S1206, the error monitoring apparatus 1200 may transmit error information of a first mobility to the traffic control server 1210 (S1208).

Herein, the analysis may mean comparing the amplitude of the ERP, which is collected for the predetermined time, and a predetermined threshold. In addition, the analysis may mean determining whether or not the amplitude of the ERP is within a predetermined threshold range during a predetermined time interval.

Meanwhile, the analysis may be preceded by a process of cognizing the onset of an ERP by using a time when a characteristic of a brain wave signal appears and/or using a pattern of a brain wave signal. In addition, the analysis may include a process of extracting an ERP.

Here, the predetermined threshold may be differently determined according to at least one of a type of the ERP and a passenger from whom the ERP is obtained.

In addition, error information of the first mobility may include time information regarding when an ERP occurs for at least one passenger in the first mobility, a waveform of the ERP, and location information or operational information of the first mobility.

Meanwhile, the traffic control server 1210 may receive error information of a first mobility from the error monitoring apparatus 1200 (S1208).

In addition, the traffic control server 1200 may determine a degree of responsibility for a first event occurring to a first mobility on the basis of error information of the first mobility (S1212). Alternatively, the traffic control server 1210 may select at least one second mobility different from a first mobility and determine a degree of responsibility for a first event between the first mobility and the second mobility.

Figure 13:
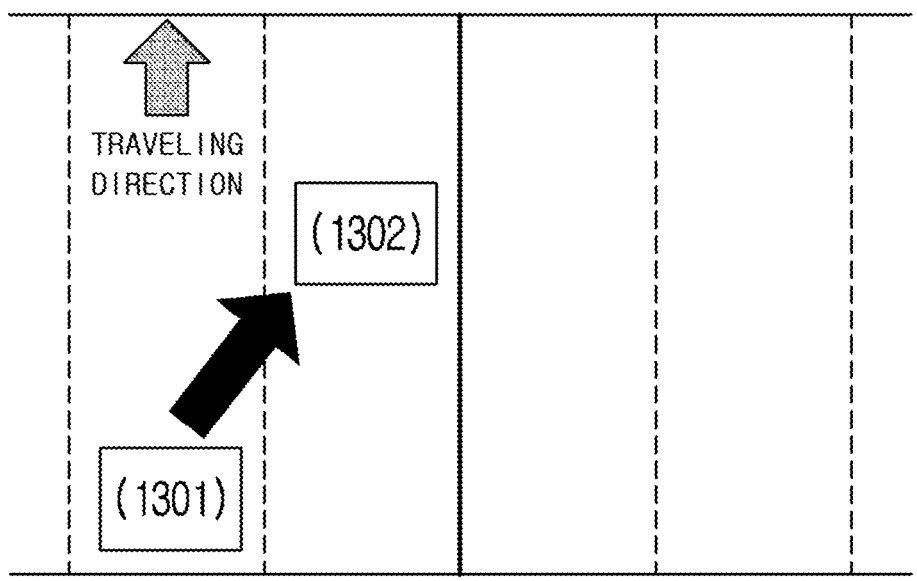
FIG. 13 is a view illustrating an operation of a traffic accident analysis system when a first mobility collides with a preceding second mobility, in one form of the present disclosure.

FIG. 13 is a view illustrating an operation of a traffic accident analysis system when a first mobility collides with a preceding second mobility, according to an embodiment of the present disclosure.

Referring to FIG. 13, it is assumed that a first mobility 1301 collides with a preceding second mobility 1302 traveling in the same direction (hereinafter, referred to as 'rear-end collision').

An error monitoring apparatus of the present disclosure may determine whether or not a rear-end collision has occurred to the first mobility 1301. Here, whether or not the rear-end collision has occurred may be determined based on a speed measuring unit, an image acquisition unit, a sound acquisition unit, a wheel monitoring unit and/or a manipulation apparatus unit, which are included in the first mobility 1301.

In addition, an error monitoring apparatus may collect an ERP from at least one passenger in the first mobility 1301 for a predetermined time. The ERP may have been consecutively or periodically measured and stored since before the rear-end collision. The error monitoring apparatus may store a display time of the ERP, location information of the first mobility 1301, etc. In addition, the error monitoring apparatus may also store a waveform of the ERP, operational information of the first mobility 1301, etc.

In addition, the error monitoring apparatus may transmit the collected and stored information to a traffic control server. For example, a traffic control server may be a traffic control center server of a district police station.

A traffic control server of the present disclosure may determine a degree of responsibility of the first mobility 1301 colliding with the second mobility 1302 by using information received from the error monitoring apparatus. Particularly, the traffic control server may identify a traffic accident occurring to the first mobility on the basis of the received information. In other words, it may determine a location and time of a traffic accident.

In addition, a traffic control server of the present disclosure may further receive error information from a mobility that is different from the first mobility 1301. Referring to FIG. 13, a traffic control server may further receive error information of the second mobility 1302 from the second mobility 1302. In addition, a traffic control server may identify a traffic accident occurring to the second mobility 1302 and determine whether or not the traffic accident occurring to the second mobility 1302 is the same as a traffic accident occurring to the first mobility 1301.

A traffic accident analysis system of the present disclosure may determine responsibility information of a traffic accident between the first mobility 1301 and the second mobility 1302, to which the traffic accident commonly occurs. In other words, a traffic accident analysis system may analyze the traffic accident situation more closely from a driver's or a passenger's point of view, from whom an ERP is displayed.

For example, the degree of responsibility may be proportional to a peak value of ERP of a first mobility and a peak value of ERP of a second mobility.

For another example, the degree of responsibility may be determined based on a time point when an ERP of a first mobility and an ERP of a second mobility are displayed.

Meanwhile, the second mobility 1302 may not have a same driving direction as the first mobility 1301 and may not precede the first mobility 1301. Irrespective of a driving direction or a driving speed, various situations may be included where the first mobility 1301 collides with the second mobility 1302.

According to the present disclosure, a traffic accident analysis system may be provided.

Also, according to the present disclosure, a traffic accident analysis system that determines primary responsibility for a traffic accident between mobilities on the basis of error monitoring may be provided.

Also, according to the present disclosure, an error monitoring apparatus and method may be provided.

Also, according to the present disclosure, a traffic control server determining primary responsibility for a traffic accident between mobilities on the basis of error monitoring and an operating method thereof may be provided.

Effects obtained in the present disclosure are not limited to the above-mentioned effects, and other effects not mentioned above may be clearly understood by those skilled in the art from the following description.

Although exemplary methods of the present disclosure are described as a series of operation steps for clarity of a description, the present disclosure is not limited to the sequence or order of the operation steps described above. The operation steps may be simultaneously performed, or may be performed sequentially but in different order. In order to implement the method of the present disclosure, additional operation steps may be added and/or existing operation steps may be eliminated or substituted.

Various forms of the present disclosure are not presented to describe all of available combinations but are presented to describe only representative combinations. Steps or elements in various forms may be separately used or may be used in combination.

In addition, various forms of the present disclosure may be embodied in the form of hardware, firmware, software, or a combination thereof. When the present disclosure is embodied in a hardware component, it may be, for example, an application specific integrated circuit (ASIC), a digital signal processor (DSP), a digital signal processing device (DSPD), a programmable logic device (PLD), a field programmable gate array (FPGA), a general processor, a controller, a microcontroller, a microprocessor, etc.

The scope of the present disclosure includes software or machine-executable instructions (for example, operating systems (OS), applications, firmware, programs) that enable methods of various forms to be executed in an apparatus or on a computer, and a non-transitory computer-readable medium storing such software or machine-executable instructions so that the software or instructions can be executed in an apparatus or on a computer.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. An error monitoring apparatus, the apparatus comprising:
    a detector configured to determine whether or not a predetermined event has occurred to a first mobility;
    a sensor configured to collect an event-related potential (ERP) for at least one passenger of the first mobility for a predetermined amount of time;
    an analyzer configured to analyze the collected ERP based on the determination; and
    a transmitter configured to send error information of the first mobility to a traffic control server that is configured to determine a degree of responsibility for the predetermined event occurring to the first mobility based on an analysis result,
    wherein the predetermined event comprises a traffic accident at least related to the first mobility,
    wherein the error information of the first mobility comprises at least one of time information regarding when the ERP occurs, a waveform of the ERP, location information of the first mobility, or operational information of the first mobility,
    wherein the ERP is a change of an electrical signal in a brain in association with a stimulus from outside or a psychological process inside,
    wherein the sensor comprises at least one of a speed measuring unit, an image acquisition unit, a sound acquisition unit, a wheel monitoring unit, or a manipulation apparatus unit, which are included in the first mobility,
    wherein the speed measuring unit measures at least one of a speed and a direction of the first mobility,
    the image acquisition unit monitors a distance between the first mobility and an object that is different from the first mobility,
    the sound acquisition unit acquires a sound generated from at least one of the inside and the outside of the first mobility,
    the wheel monitoring unit may monitor at least one level of a temperature and a pressure inside a wheel of the first mobility,
    the manipulation apparatus unit monitors a pressure upon at least one of a steering wheel, an accelerator pedal, and a brake of the first mobility,
    wherein the detector is configured to determine, by applying a predetermined threshold to at least one of the speed measuring unit, the image acquisition unit, the sound acquisition unit, the wheel monitoring unit, or the manipulation apparatus unit, whether or not the predetermined event has occurred to the first mobility,
    wherein the predetermined threshold is a value set by a user input or a predefined value, and
    wherein a magnitude of the predetermined threshold is set according to the speed measuring unit, the image acquisition unit, the sound acquisition unit, the wheel monitoring unit, and the manipulation apparatus unit, respectively.

2. The error monitoring apparatus of claim 1,
    wherein the ERP comprises at least one of error-related negativity (ERN), error positivity (Pe), correct-related negativity (CRN), or correct positivity (Pc).

3. The error monitoring apparatus of claim 1, wherein the detector is configured to:
    determine a predetermined threshold differently according to at least one of a type of the ERP or a passenger from whom the ERP is obtained.

4. The error monitoring apparatus of claim 1, wherein the transmitter is configured to:
    transmit error information of the first mobility to the traffic control server when an amplitude of the collected ERP exceeds the predetermined threshold range.

5. A traffic control server comprising:
    a receiver configured to receive error information of a first mobility from the first mobility; and
    a controller configured to determine a degree of responsibility for a first event occurring to the first mobility based on the error information of the first mobility,
    wherein the first event comprises a traffic accident at least related to the first mobility,
    wherein the error information of the first mobility comprises at least one of time information regarding when an event-related potential (ERP) for at least one passenger in the first mobility occurs, a waveform of the ERP, location information of the first mobility, or operational information of the first mobility,
    wherein the ERP is a change of an electrical signal in a brain in association with a stimulus from outside or a psychological process inside,
    wherein the first mobility comprises an error monitoring apparatus transmitting the error information of the first mobility to the traffic control server,
    wherein the error monitoring apparatus is configured to determine whether or not a predetermined event has occurred to the first mobility by a detector, collect the ERP for at least one passenger of the first mobility for a predetermined amount of time by a sensor, analyze the collected ERP by an analyzer, and transmit the error information of the first mobility to the traffic control server based on an analysis result by a transmitter, wherein the sensor comprises at least one of a speed measuring unit, an image acquisition unit, a sound acquisition unit, a wheel monitoring unit, or a manipulation apparatus unit, which are included in the first mobility, wherein the speed measuring unit measures at least one of a speed and a direction of the first mobility, the image acquisition unit monitors a distance between the first mobility and an object that is different from the first mobility, the sound acquisition unit acquires a sound generated from at least one of the inside and the outside of the first mobility, the wheel monitoring unit may monitor at least one level of a temperature and a pressure inside a wheel of the first mobility, the manipulation apparatus unit monitors a pressure upon at least one of a steering wheel, an accelerator pedal, and a brake of the first mobility, wherein the detector is configured to determine, by applying a predetermined threshold to at least one of the speed measuring unit, the image acquisition unit, the sound acquisition unit, the wheel monitoring unit, or the manipulation apparatus unit, whether or not the predetermined event has occurred to the first mobility, wherein the predetermined threshold is a value set by a user input or a predefined value, and wherein a magnitude of the predetermined threshold is set according to the speed measuring unit, the image acquisition unit, the sound acquisition unit, the wheel monitoring unit, and the manipulation apparatus unit, respectively.

6. The traffic control server of claim 5, wherein the controller is configured to:

identify a first event occurring to the first mobility by using error information of the first mobility.

7. The traffic control server of claim 6, wherein the controller is further configured to:

obtain information related to the first event from another image acquisition unit that is installed within a predetermined range around a location of the first mobility; and identify the first event occurring to the first mobility by using the obtained information and the error information of the first mobility, wherein the another image acquisition unit is installed outside of the first mobility and obtains image and sound information relating to the first event.

8. The traffic control server of claim 6, wherein the receiver is further configured to:

receive error information of at least one second mobility from the second mobility that is different from the first mobility, and wherein the controller is configured to:

identify, by using the error information of the second mobility, a second event occurring to the second mobility; and select a second mobility related to the first event based on the identified second event.

9. The traffic control server of claim 8, wherein, when the second event is the same as the first event, the controller is configured to select a second mobility to which the second event occurs.

10. The traffic control server of claim 7, wherein the controller is configured to:

determine a degree of responsibility for an onset of the first event between the first mobility and the selected second mobility.

11. The traffic control server of claim 10, wherein the degree of responsibility is proportional to a peak value of ERP of the first mobility and a peak value of ERP of the second mobility.

12. A traffic accident analysis system, the system comprising:

an error monitoring apparatus transmitting error information of a mobility to a traffic control server, the error monitoring apparatus configured to:

determine whether or not a predetermined event has occurred to a first mobility by a detector;

collect an event-related potential (ERP) for at least one passenger of the first mobility for a predetermined amount of time by a sensor;

analyze the collected ERP based on the determination by an analyzer; and transmit the error information of the first mobility to the traffic control server based on an analysis result by a transmitter; and a traffic control server determining a degree of responsibility for an onset of a predetermined event between mobilities by using the error information of the mobility, the traffic control server being configured to:

receive the error information of the first mobility from the monitoring apparatus; and determine a degree of responsibility for a first event occurring to the first mobility, wherein the predetermined event comprises a traffic event that is related at least to the first mobility, wherein the error information of the first mobility comprises at least one of time information regarding when the ERP occurs, a waveform of the ERP, location information of the first mobility, or operational information of the first mobility, wherein the ERP is a change of an electrical signal in a brain in association with a stimulus from outside or a psychological process inside, wherein the sensor comprises at least one of a speed measuring unit, an image acquisition unit, a sound acquisition unit, a wheel monitoring unit, or a manipulation apparatus unit, which are included in the first mobility, wherein the speed measuring unit measures at least one of a speed and a direction of the first mobility, the image acquisition unit monitors a distance between the first mobility and an object that is different from the first mobility, the sound acquisition unit acquires a sound generated from at least one of the inside and the outside of the first mobility, the wheel monitoring unit may monitor at least one level of a temperature and a pressure inside a wheel of the first mobility, the manipulation apparatus unit monitors a pressure upon at least one of a steering wheel, an accelerator pedal, and a brake of the first mobility, wherein the detector is configured to determine, by applying a predetermined threshold to at least one of the speed measuring unit, the image acquisition unit, the sound acquisition unit, the wheel monitoring unit, or the manipulation apparatus unit, whether or not the predetermined event has occurred to the first mobility, wherein the predetermined threshold is a value set by a user input or a predefined value, and wherein a magnitude of the predetermined threshold is set according to the speed measuring unit, the image acquisition unit, the sound acquisition unit, the wheel monitoring unit, and the manipulation apparatus unit, respectively.

13. The traffic accident analysis system of claim 12, wherein the traffic control server is configured to:
receive error information of at least one second mobility from the second mobility that is different from the first mobility;
identify a second event occurring to the second mobility by using error information of the second mobility;
select a second mobility with a second event that is the same as the first event; and
determine a degree of responsibility for the first event between the first mobility and the selected second mobility.

14. The traffic accident analysis system of claim 13, wherein the degree of responsibility is proportional to a peak value of ERP of the first mobility and a peak value of ERP of the second mobility.

15. An error monitoring method, the method comprising:
determining whether or not a predetermined event has occurred to a first mobility;
sensing to collect an event-related potential (ERP) for at least one passenger of the first mobility for a predetermined amount of time;
analyzing the collected ERP based on the determination; and
transmitting error information of the first mobility to a traffic control server that is configured to determine a degree of responsibility for the predetermined event occurring to the first mobility based on an analysis result,
wherein the predetermined event comprises a traffic accident related at least to the first mobility,
wherein the error information of the first mobility comprises at least one of time information regarding when the ERP occurs, a waveform of the ERP, location information of the first mobility, or operational information of the first mobility,
wherein the ERP is a change of an electrical signal in a brain in association with a stimulus from outside or a psychological process inside,
wherein the sensing is performed by at least one of a speed measuring unit, an image acquisition unit, a sound acquisition unit, a wheel monitoring unit, or a manipulation apparatus unit, which are included in the first mobility,
wherein the speed measuring unit measures at least one of a speed and a direction of the first mobility,
the image acquisition unit monitors a distance between the first mobility and an object that is different from the first mobility,
the sound acquisition unit acquires a sound generated from at least one of the inside and the outside of the first mobility,
the wheel monitoring unit may monitor at least one level of a temperature and a pressure inside a wheel of the first mobility,
the manipulation apparatus unit monitors a pressure upon at least one of a steering wheel, an accelerator pedal, and a brake of the first mobility,
wherein the method further comprises determining whether or not the predetermined event has occurred to the first mobility by applying a predetermined threshold to at least one of the speed measuring unit, the image acquisition unit, the sound acquisition unit, the wheel monitoring unit, or the manipulation apparatus unit,
wherein the predetermined threshold is a value set by a user input or a predefined value, and
wherein a magnitude of the predetermined threshold is set according to the speed measuring unit, the image acquisition unit, the sound acquisition unit, the wheel monitoring unit, and the manipulation apparatus unit, respectively.

16. The error monitoring method of claim 15, wherein the method comprises:
when an amplitude of the collected ERP exceeds a predetermined threshold range, transmitting error information of the first mobility to the traffic control server,
wherein the ERP comprises at least one of error-related negativity (ERN), error positivity (Pe), correct-related negativity (CRN), or correct positivity (Pc).

* * * * *